(12) United States Patent
Johnson et al.

(10) Patent No.: US 7,687,690 B2
(45) Date of Patent: Mar. 30, 2010

(54) RICE MUTANT ALLELE

(75) Inventors: Carl W. Johnson, Chico, CA (US);
Kent S. McKenzie, Oroville, CA (US)

(73) Assignee: California Cooperative Rice Research Foundation, Inc., Biggs, CA (US)

( * ) Notice: Subject to any disclaimer, the term of this patent is extended or adjusted under 35 U.S.C. 154(b) by 266 days.

(21) Appl. No.: 11/846,604

(22) Filed: Aug. 29, 2007

(65) Prior Publication Data

US 2009/0064356 A1  Mar. 5, 2009

(51) Int. Cl.
*A01H 1/00* (2006.01)
*A01H 1/02* (2006.01)
*A01H 5/00* (2006.01)
*A01H 5/10* (2006.01)
*C12N 5/04* (2006.01)

(52) U.S. Cl. .................... 800/320.2; 800/260; 800/265; 800/269; 800/274; 800/277; 800/278; 800/300; 800/303; 800/279; 435/421; 435/430; 435/430.1

(58) Field of Classification Search ................ None
See application file for complete search history.

(56) References Cited

U.S. PATENT DOCUMENTS

| 4,351,130 | A | 9/1982 | Rutger et al. |
| 6,911,589 | B2 * | 6/2005 | Johnson .................. 800/320.2 |
| 7,138,567 | B2 | 11/2006 | Okawa et al. |

\* cited by examiner

*Primary Examiner*—Medina A Ibrahim
(74) *Attorney, Agent, or Firm*—Jondle & Associates, P.C.

(57) ABSTRACT

A rice mutant allele designated phd is disclosed. The invention relates to rice seeds containing mutant allele phd, to rice plants containing allele phd and to methods for producing a rice plant containing the mutant allele phd produced by crossing a rice plant containing allele phd with itself or another rice variety. The invention further relates to hybrid rice seeds and hybrid rice plants containing mutant allele phd.

21 Claims, No Drawings

RICE MUTANT ALLELE

BACKGROUND OF THE INVENTION

This invention relates to a rice plant, seed, variety and hybrid. More specifically, the present invention relates to a rice plant mutant allele designated "phd". The mutant allele, phd, contributes to improved emergence of rice seedlings, improved stand establishment after seeding, improved weed competition, tolerance to rice herbicides, and grain quality and yield. All publications cited in this application are herein incorporated by reference.

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. Another method of planting by the dry-seeded system is to broadcast the seed by airplane into a flooded field, then promptly drain the water from the field. For the dry-seeded system, when the plants have reached sufficient size (four- to five-leaf stage), a shallow permanent flood of water 5 to 16 cm deep is applied to the field for the remainder of the crop season. It is a desirable to have rice varieties that grow quickly as seedlings to compete with weeds and hasten the application of a permanent flood that suppresses the growth of grassy weeds.

In the water-seeded system, rice seed is soaked for 12 to 36 hours to initiate germination, and the seed is broadcast by airplane into a flooded field. This is the predominant rice production system in California. Before the advent of grass herbicides, rice growers would use deep water (20-30 cm) for grassy weed control. Beginning in the mid-1970's adapted semidwarf rice cultivars became available in California. There was concern that semidwarf cultivars would not emerge through deep water and it was unknown what a reasonable water depth would be for stand establishment. Extensive rice seedling vigor research and breeding has been conducted by the University of California, USDA-ARS, and cooperating scientists at California Cooperative Rice Research Foundation. It was found that older tall varieties as a group emerged through deep water 3-4 days before the semidwarf lines. Dat et al., reported that the tall rice showed 7% greater seedling height than semidwarf rice in their field studies (*Crop Sci* 18:1 (1978)). McKenzie et al., conducted seedling vigor tests of near isogenic lines and reported that tall lines as a group showed higher emergence percentage (*Crop. Sci*. 20:169 (1980). At shallow water depths the tall varieties came through first but not to the statistically significant level observed in deep water. Yield advantages of the semidwarf plant type were very significant. Through the use of grass herbicides, precision leveling, and plant breeding for improved seedling vigor in semidwarf cultivars, the tall varieties were rapidly replaced in California.

The rice seedlings emerge through a shallow flood, or the water may be drained from the field for a short period of time to enhance seedling establishment. Lowering the water improves stand establishment and exposes weeds for contact herbicide applications. However this promotes grassy weed growth, nitrogen loss, and increased water consumption and management. Herbicide use on rice can injure the rice plant, reduce plant growth, shorten the height, delay maturity of the plant and possibly reduce yield. In recent years, due to environmental regulations, appearance of herbicide resistant weeds, phasing out of older herbicides, and increased organic rice production, interest in using deeper water levels to aid weed control has increased. Rice breeders continue to select for improved seedling vigor although incremental improvements have been difficult to incorporate with the agronomic and quality traits demanded by growers and marketers.

A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium grain and short-grain. Typical U.S. long-grain cultivars cook dry and fluffy when steamed or boiled, whereas medium- and short-grain cultivars cook moist and sticky. Long-grain cultivars have been traditionally grown in the southern states and generally receive higher market prices.

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

Grain weight is a very important yield component in rice. Genetic control of grain weight is typically quantitatively inherited. Large kernel size is often a desirable quality feature.

There are some important traits in rice that are controlled by single genes or genes of major effect and are simply inherited. One of the most notable is the semidwarf habit that is controlled by the sd gene. This gene has been used extensively to produce high yielding short stature rice varieties and has been the subject of extensive research, including the actual sequencing of the gene and the various alleles. Another single gene trait, elongated upper internode, eui, has been identified as a useful trait (Rutger and Carnahan *Crop Sci*. 21:373 (1981); Mackill et al., *SABRAO* 26:11 (1994); Shen and He *Proc. 6$^{th}$ Int. SABRAO Congr.* 753 (1989)) and is used in hybrid rice production (Virmani et al., Int. Rice Res. Notes 3:6 (1988)).

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better agronomic characteristics on grain quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of rice plant breeding is to develop new, unique and superior rice cultivars and hybrids. The breeder initially selects and crosses two or more parental lines, followed by self-pollination and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same rice traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice cultivars.

The development of new rice cultivars requires the development and selection of rice varieties, the crossing of these varieties and selection of superior hybrid crosses. The hybrid seed is produced by manual crosses between selected male-fertile parents or by using male sterility systems. These hybrids are selected for certain single gene traits such as semi-dwarf plant type, pubescence, awns, and apiculus color which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Rice, *Oryza sativa* L., is an important and valuable field crop. Thus, a continuing goal of rice plant breeders is to develop stable, high yielding rice cultivars that are agronomically sound. The reasons for this goal are obviously to maximize the amount of grain produced on the land used and to supply food for both animals and humans. To accomplish this goal, the rice breeder must select and develop rice plants that have the traits that result in superior cultivars.

The foregoing examples of the related art and limitations related therewith are intended to be illustrative and not exclusive. Other limitations of the related are will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above described problems have been reduced or eliminated, while other embodiments are directed to other improvements.

The present invention relates to a rice mutant allele, designated "phd", for plant height discovery. The present invention also relates to a rice seed, a rice plant, a rice cultivar, and a rice hybrid containing the phd allele. This mutant allele has been determined to be a single recessive gene. The invention further provides plants, seeds, and other plant parts such as pollen and ovules containing the mutant allele. In addition the present invention is directed to transferring the phd allele to other rice cultivars and species and is useful for producing rice cultivars and novel types with the phd trait.

The invention also provides methods for introducing the allele of the present invention into rice plants by crossing a rice plant which lacks the mutant allele with a rice plant that has the allele, selfing the resulting generations and then selecting the plants exhibiting one or more of the following: increased length of leaves, stem internodes and/or panicles and an increase in grain size of the rice plant.

In another aspect, the invention provides a method for producing a hybrid rice seed comprising crossing a first plant parent with a second plant parent and harvesting the resultant hybrid rice seed, wherein either one or both parents contain phd, the mutant allele. The hybrid seeds, plant and parts thereof produced by such method are also part of the invention.

In another aspect, the present invention provides for single gene converted plants containing the mutant allele phd. The desired single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring rice gene or a transgene introduced through genetic engineering techniques.

In another aspect, the present invention provides regenerable cells for use in tissue culture of rice plant containing phd. The tissue culture will preferably be capable of regenerating plants having the physiological and morphological characteristics of the foregoing rice plant, and of regenerating plants having substantially the same genotype as the foregoing rice plant. Preferably, the regenerable cells in such tissue cultures will be embryos, protoplasts, meristematic cells, callus, pollen, leaves, anthers, pistils, roots, root tips, flowers, seeds, panicles or stems. Still further, the present invention provides rice plants regenerated from the tissue cultures of the invention.

Another aspect of the invention relates to any rice seed or plant having the mutant allele phd.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Alter. The utilization of up-regulation, down-regulation, or gene silencing.

Backcrossing. Backcrossing is a process in which a breeder successively crosses hybrid progeny back to one of the parents, for example, a first generation hybrid $F_1$ with one of the parental genotypes of the $F_1$ hybrid.

Cell. Cell as used herein includes a plant cell, whether isolated, in tissue culture or incorporated in a plant or plant part.

Cotyledon. A cotyledon is a type of seed leaf. The cotyledon contains the food storage tissues of the seed.

Culm. The culm is the plant stem. It contains nodes and internodes. The internodes elongate as the plant matures pushing the younger leaves and ultimately pushing the inflorescence out through the leaf sheath of the flag leaf.

Days to 50% heading. Average number of days from planting to the day when 50% of all panicles are exerted at least partially through the leaf sheath. A measure of maturity.

DW-206. DW-206, (for deep water M-206), is the formerly used name for the mutant allele phd. The two names, DW-206 and phd, both represent the exact same allele which was deposited with the American Type Culture Collection (ATCC) under the Accession Number PTA-8541. Some of the documents submitted to ATCC indicate DW-206 which is the exact same allele as that of the present invention, phd.

Embryo. The embryo is the small plant contained within a mature seed.

Essentially all the physiological and morphological characteristics. A plant having essentially all the physiological and morphological characteristics means a plant having the physiological and morphological characteristics of the cultivar, except for the characteristics derived from the converted gene.

Flag Leaf. The flag leaf is the last leaf to emerge from the culm and is located just below the panicle. It consists of a sheath that is wrapped around the stem and a flat blade that extends from the sheath.

Gene Silencing. Gene silencing refers to the interruption or suppression of the expression of a gene at the level of transcription or translation.

Genotype. Genotype refers to the genetic constitution of a cell or organism.

Grain Length (L). The length of a rice grain is measured in millimeters.

Grain Width (W). The width of a rice grain is measured in millimeters.

Grain Yield. Grain yield is measured in pounds per acre and at 14.0% moisture. Grain yield of rice is determined by the number of panicles per unit area, the number of fertile florets per panicle, and grain weight per floret.

Harvest Moisture. Harvest moisture refers to the percent of moisture of the grain when harvested.

Hypocotyl. A hypocotyl is the portion of an embryo or seedling between the cotyledons and the root. Therefore, it can be considered a transition zone between shoot and root.

Leaf. The rice leaf consist of a sheath and a blade (lamina). The leaf sheath is an elongated part of the leaf rolled into a cylinder that encloses the developing new leaves and stem at later growth stages. The basal portion of the leaf sheath is attached to a nodal plate. The leaf blade is long and lanceolate with a midrib and has parallel veins on each side.

Leaf length. Leaf length is measured by measuring the longitudinal distance in centimeters of the mature rice leaf. Leaf blade length is the measured distance for the blade in centimeters from the attachment to the leaf sheath to the tip of the leaf.

Length/Width (L/W) Ratio. This ratio is determined by dividing the average grain length (L) by the average grain width (W).

Locus. A locus confers one or more traits such as, for example, male sterility, herbicide tolerance, insect resistance, disease resistance, and improved yield. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Lodging Resistance (also called Straw Strength). Lodging is measured as a subjective rating and is a percentage of the plant stems leaning or fallen completely to the ground before harvest. It is a relative scale.

1000 Grain Wt. 1000 grain weight refers to the weight of 1000 rice grains as measured in grams. 1000 grain weight may be measured according to the form of rice including paddy (with hull), brown (without hull) or milled rice (without hull, germ and bran).

Panicle. Panicle refers to the inflorescence of the rice plant.

Panicle Length. Panicle length is the length of the rice panicle in centimeters from the base of the panicle to the tip of the panicle.

Plant. As used herein, the term "plant" includes reference to an immature or mature whole plant, including a plant from which seed or grain or anthers have been removed. A seed or embryo that will produce the plant is also considered to be the plant.

Plant Height. Rice plant height is measured in centimeters from soil surface to the tip of the extended panicle at harvest.

Plant Parts. As used herein, the term "plant parts" (or a rice plant, or a part thereof) includes protoplasts, leaves, stems, roots, root tips, anthers, pistils, seed, grain, embryo, pollen, ovules, cotyledon, hypocotyl, panicles, flower, shoot, tissue, petiole, cells, meristematic cells and the like.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Seedling Emergence. Seedling emergence is the point at which the tip of the leaf of the growing rice seedling leaf emerges through the water in water seeded rice or the soil in direct seeded rice. This may be measured in days from planting to seedling emergence and will be the number or percentage of seedlings that have emerged.

Seedling Vigor. Seedling vigor refers to the ability of the seedling to emerge rapidly through the soil or water after planting. It is frequently measured by visual observation field test and assigned a relative score.

Single Gene Converted (Conversion). Single gene converted (conversion) plant refers to plants which are developed by a plant breeding technique called backcrossing with selection wherein essentially all of the desired morphological and physiological characteristics of a variety are recovered in addition to the single gene transferred into the variety via the backcrossing technique or via genetic engineering.

Stem Internode Length. Stem internode length is the longitudinal distance of an elongated internode (section of the stem between consecutive nodes) measured in centimeters.

Upper Internode Length. Upper internode length is the longitudinal distance in centimeters of the last fully elongated internode that is located just below the panicle.

DETAILED DESCRIPTION OF THE INVENTION

The present invention is a new rice plant height allele which improves emergence of rice seedlings in flooded rice fields and other uses. The present invention relates to a new and distinctive rice mutant allele designated "phd". This mutant was first identified in a seed field of the rice cultivar 'M-206' (U.S. Pat. No. 6,911,589 to Johnson issued Jun. 28, 2005).

According to the invention, there is provided a novel rice mutant allele designated "phd" that results in part one or more of the following phenotypic characteristics: increased length of leaves, stem internodes and/or panicles and an increase in grain size of the rice plant. This invention thus relates to rice seeds containing the phd allele, to rice plants containing the phd allele and to methods for producing a rice plant by crossing a rice plant containing the phd allele with itself or another rice line.

Thus, any such methods using rice containing the phd allele are part of this invention: selfing, backcrosses, hybrid production, crosses to populations, and the like. All plants produced using rice containing the phd allele as a parent are within the scope of this invention.

EXAMPLES

The following examples are provided to further illustrate the present invention and are not intended to limit the invention beyond the limitations set forth in the appended claims.

Example 1

Three plants were selected from the M-206 foundation field in Biggs, Calif. in 2004. Eleven panicle rows of rice plants containing the mutant allele of the present invention were grown in the 2005 breeding nursery in comparison with the parent cultivar M-206 and spontaneous mutants of M-206 with the eui trait (elongated upper internode; Rutger and Carnahan *Crop Sci.* 21:373 (1981)) as a check. The rows of M-206 plants containing the phd mutant allele were uniformly noted to be later heading (3 days) and were 15 cm taller than M-206. At maturity the mutant phd plant rows were 20 cm taller than the M-206 parent. However, the phd mutant allele plants did not have the elongated upper internode characteristic of the M-206 plants with the eui trait and were different from the M-206 plants with the eui trait as well as other rice plants that had been observed with the eui trait. Progeny tests revealed that the plants containing the mutant allele of the present invention had increased leaf and stem internode lengths, produced larger grains and showed improved seeding emergence in water-seeded tests. The plant height difference was also passed on to the progeny. This was again confirmed in the progeny grown in the nursery 2006 and 2007 in Biggs, Calif. and the 2006-2007 rice winter nursery in Kauai, Hi. Data show that plant heights of the mutant allele phd plants were being controlled by a different gene than the $sd_1$ allele found in M-206 and also different than that of the M-206 plants that have the eui trait.

A longer leaf and taller plant and enhanced stand establishment unexpectedly provided increased competition with weeds and provided improved seedling vigor and emergence for the rice seedlings. The taller plants unexpectedly provide improved tolerance to some rice herbicides that normally injure and shorten rice plant height. The plants containing the mutant allele phd of the present invention unexpectedly still have the benefits of the productive $sd_1$ gene widely used in modern rice cultivars. In addition, there were some additional characteristics associated with phd including increased grain size and weight and a later (3-4 days) heading date.

Example 2

Seed of rice cultivar M-206 containing the phd allele of the present invention were grown for advancement, increase, and testing in the nursery at Biggs, Calif. in 2006 Results of culm measurements from 2006 are summarized Table 1. Table 1 illustrates the increased leaf length and stem internode length of plants containing the phd allele over M-206 but there is a reduced upper internode length compared to the M206 plants with the eui trait. In Table 1, column 1 shows the plant characteristic, column 2 shows the measurements of the characteristic for M-206 rice plants containing the mutant allele of the present invention, phd, column 3 shows the measurements of the characteristics for rice cultivar M-206, column 4 shows the percent difference between M-206 and M-206 plants containing the mutant allele of the present invention, phd, column 5 shows the measurements of the characteristic for M-206 rice plants containing the mutant allele of the present invention phd, column 6 shows the measurements of the characteristics for M-206 rice plants containing eui, and column 7 shows the percent difference between M-206 rice plants containing eui and M-206 rice plants containing the mutant allele of the present invention, phd. Percent difference was calculated by, for example, subtracting the value for M-206 from the value for an M-206 plant containing phd and then dividing by the value for M-206 and multiplying the resulting value by 100. In Table 1, flag leaf blade-1=$1^{st}$ leaf below flag leaf, flag blade leaf-2=$2^{nd}$ leaf blade below flag leaf, flag leaf blade-3=$3^{rd}$ leaf blade below flag leaf, Internode-1=$1^{st}$ Internode below upper internode, Internode-2=$2^{nd}$ internode below upper internode, Internode-3=$3^{rd}$ internode below upper internode, and Internode-4=$4^{th}$ internode below upper internode.

Unexpectedly, internodes 1 and 2 and the flag leaf blade and flag leaf blade-1 were significantly longer in M-206 rice plants containing mutant allele phd than in M-206. Also, surprisingly, M-206 plants with the mutant allele phd of the present invention did not have the elongated upper internode characteristic of M-206 plants with the eui trait. The elongated upper internode trait, eui, causes the ripening panicles to droop and the plants to lodge but this was not the case for the M-206 plants with the mutant allele phd of the present invention.

TABLE 1

| Characteristic | M-206 Plants w/phd | M-206 | % Diff | M-206 Plants w/phd | M-206 Plants w/eui | % Diff |
| --- | --- | --- | --- | --- | --- | --- |
| Grains/panicle | 132 | 135 | −2 | 132 | 176 | −25 |
| Panicle length (cm) | 26.1 | 23 | 14 | 26.1 | 26.2 | −0 |
| Flag leaf blade (cm) | 37.2 | 33.5 | 11 | 37.2 | 34.7 | 7 |
| Upper Internode (cm) | 37.6 | 37.1 | 1 | 37.6 | 56.4 | −33 |

TABLE 1-continued

| Characteristic | M-206 Plants w/phd | M-206 | % Diff | M-206 Plants w/phd | M-206 Plants w/eui | % Diff |
|---|---|---|---|---|---|---|
| Flag leaf blade-1 (cm) | 41.8 | 38.5 | 9 | 41.8 | 41.2 | 2 |
| Internode-1 (cm) | 23.4 | 15.2 | 54 | 23.4 | 18.9 | 24 |
| Flag leaf blade-2 (cm) | 41.6 | 40.3 | 3 | 41.6 | 42.1 | −1 |
| Internode-2 (cm) | 15.2 | 11.7 | 30 | 15.2 | 13.2 | 16 |
| Flag leaf blade-3 (cm) | 38 | 37 | 3 | 38 | 44.9 | −15 |
| Internode-3 | 8.6 | 4.2 | 105 | 8.6 | 9.2 | −6 |
| Internode-4 | 1.5 | 1 | 50 | 1.5 | 1.8 | −16 |

Example 3

Table 2 contains grain characteristic data showing the increased grain size of the rice plants containing the phd mutant allele. Measurements were collected using a flatbed scanner (Winseedle Software) on an 80 kernel sample for rice cultivar M-206 and for rice plants containing mutant allele phd. In Table 2, column 1 shows the type of rice and the grain characteristic, column 2 shows the measurements for the characteristics for rice plants containing mutant allele phd, column 3 shows the measurements for the characteristics for rice cultivar M-206 and column 4 shows the percent difference between rice cultivar M-206 and rice plants containing mutant allele phd. Projected area=two dimensional area of the scanned image in square millimeters.

TABLE 2

| Grain Characteristic | M-206 Plants w/allele phd | M-206 | % Diff |
|---|---|---|---|
| Paddy Rice | | | |
| Length (mm) | 9.09 | 8.80 | 3.30 |
| Width (mm) | 3.39 | 3.30 | 2.73 |
| Projected area (mm$^2$) | 23.20 | 21.30 | 8.92 |
| 1000 grain weight (g) | 32.90 | 31.00 | 6.13 |
| Brown Rice | | | |
| Length (mm) | 6.64 | 6.24 | 6.41 |
| Width (mm) | 2.86 | 2.84 | 0.70 |
| Projected area (mm$^2$) | 15.70 | 14.40 | 9.03 |
| 1000 grain weight (g) | 26.60 | 24.40 | 9.02 |
| Milled Rice | | | |
| Length (mm) | 6.41 | 6.08 | 5.43 |
| Width (mm) | 2.84 | 2.79 | 1.79 |
| Projected area (mm$^2$) | 14.30 | 13.20 | 8.33 |
| 1000 grain weight (g) | 25.00 | 22.80 | 9.65 |

Example 4

Seedling vigor tests with M-206 rice plants containing mutant allele phd and rice cultivar M-206 were conducted at Biggs, Calif. in 2007. Table 3 shows the results of visual seedling vigor sores for plants containing mutant allele phd and M-206 in a water-seeded large plot yield test. M-206 plants containing phd were rated a higher score in all four replications than M-206 plants. The rating is a visual seedling vigor score where 1=poor and 5=excellent. Column 1 shows the repetition, column 2 shows the seeding date, column 3 shows the scores for rice cultivar M-206 and column 4 shows the scores for M-206 plants containing mutant allele phd.

TABLE 3

| Reps | Seeding date | M-206 | M-206 plants w/phd |
|---|---|---|---|
| Rep 1 | May 15, 2007 | 4.7 | 4.9 |
| Rep 2 | May 15, 2007 | 4.8 | 5.0 |
| Rep 3 | May 23, 2007 | 4.9 | 5.0 |
| Rep 4 | May 23, 2007 | 4.9 | 5.0 |
| Avg. | | 4.8 | 5.0 |

Example 6

In an experiment comparing seedling stand-establishment in deep and shallow water depths, rice plants containing mutant allele phd showed unexpectedly higher seedling emergence through the deep (22 cm) water than M-206 as shown in Table 4. Column 1 shows the rice plants, column 2 shows the water depth in centimeters, column 3 shows the percentage of plants emerged above the water on Jun. 4, 2007, column 4 shows the plant height in centimeters on Jun. 6, 2007 and column 5 shows total percentage of plants that survived and emerged by Jul. 17, 2007 in these experiments.

TABLE 4

| Plant | Water depth (cm) | % Emergence by Jun. 4, 2007 | Plant Height by Jun. 6, 2007(cm) | % Stand by Jul. 17, 2007 |
|---|---|---|---|---|
| M-206 | 10 | 61 | 23 | 77 |
| M-206 Plants w/allele phd | 10 | 61 | 23 | 79 |
| M-206 | 22 | 3 | 25 | 33 |
| M-206 Plants w/allele phd | 22 | 6 | 27 | 41 |

% Emergence is the percentage of plants that have their leaf emerged through the water on a given date after seeding. % Stand is the percentage of plants that have survived and emerged through the water. Unexpectedly, M-206 plants containing allele phd had a significantly better stand in deep water (22 cm) and even showed improvement in stand over M-206 plants lacking the allele of the present invention in shallow water (10 cm).

Example 7

Genetic tests were performed to determine if the phd allele was the result of a cross pollination of M-206 or possibly a seed contamination. Coded samples of rice cultivar M-206, plants containing mutant allele phd and plants containing the eui trait were submitted to OMIC USA Inc., for varietal identification by DNA marker analysis in 2006. Based on the analysis of the DNA samples by Simple Sequence Repeat (SSR) methods using 10 selective genetic markers it was certified that the DNA from the submitted sample of plants containing mutant allele phd matches the DNA of M-206 variety with no contamination. Therefore, mutant allele phd is a novel mutation of rice cultivar M-206.

Example 8

Inheritance studies were initiated in 2006. Rice plants containing mutant allele phd were crossed with the parent M-206, a California semidwarf ($sd_1$) medium grain rice cultivar. The resulting $F_1$ hybrid rice plants were not taller that the non-phd parent (M-206) indicating that mutant allele phd is a recessive gene. The $F_2$ populations grown in 2007 at Biggs, Calif. segregated for the phd plant height showing the trait is heritable and segregates in simple Mendelian fashion (single recessive gene). Table 5 shows the number of plants characterized as either short (semidwarf) or tall (expressing the mutant allele of the present invention, phd) of the $F_2$ population from the cross of M-206 plants containing allele phd with M-206 plants lacking allele phd. Phenotypic classification of these $F_2$ plants for short (semidwarf) or tall (phd trait) shown in Table 5 gave good fit to a 7:1 ratio indicating the phd trait is inherited as a single recessive gene.

TABLE 5

| Phenotype | Observed | Theoretical | $X^2$ for 3:1 inheritance |
|---|---|---|---|
| Short (90-110 cm) semidwarf | 251 | 242 | =0.26 |
| Tall (115-125 cm) phd allele | 72 | 81 | $0.50 < P < 0.75$ |

Table 6 shows the number of plants characterized as short (semidwarf) or tall (expressing the mutant allele of the present invention, phd) for the $F_2$ population from a backcross, (M-206 plants containing allele phd×M-206 $F_1$)×M-206. Phenotypic classification of these $F_2$ plants for short (semidwarf) or tall (phd trait) shown in Table 6 gave good fit to a 7:1 ratio indicating the phd trait is inherited as a single recessive gene.

TABLE 6

| Phenotype | Observed | Theoretical | $X^2$ for 7:1 inheritance |
|---|---|---|---|
| Short (90-110 cm) semidwarf | 320 | 224 | =0.56 |
| Tall (115-125 cm) phd allele | 50 | 46 | $0.25 < P < 0.50$ |

This invention is directed to any rice seed or plant containing the phd allele. This invention also is directed to methods for producing a rice plant by crossing a first parent rice plant with a second parent rice plant wherein either the first or second parent rice plant is a rice plant containing the phd allele. Further, both first and second parent rice plants can comprise the rice phd allele. Still further, this invention also is directed to methods for producing a rice cultivar containing the phd allele by crossing a rice cultivar containing the phd allele with a second rice plant and growing the progeny seed, and repeating the crossing and growing steps with the rice cultivar containing the phd allele from 0 to 7 times. Thus, any such methods using the rice phd allele are part of this invention: selfing, backcrosses, hybrid production, crosses to populations, and the like. All plants produced using rice plants containing the phd allele as parents are within the scope of this invention, including plants derived from rice phd. Advantageously, the rice line is used in crosses with other, different, rice line to produce first generation ($F_1$) rice seeds and plants with superior characteristics.

It should be understood that rice plants containing the phd allele can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils and the like.

Further Embodiments of the Invention

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years, several methods for producing transgenic plants have been developed, and the present invention, in particular embodiments, also relates to transformed versions of the claimed cultivar.

Culture for expressing desired structural genes and cultured cells are known in the art. Also as known in the art, rice is transformable and regenerable such that whole plants containing and expressing desired genes under regulatory control may be obtained. General descriptions of plant expression vectors and reporter genes and transformation protocols can be found in Gruber, et al., "Vectors for Plant Transformation", in *Methods in Plant Molecular Biology & Biotechnology* in Glich, et al., (Eds. pp. 89-119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement*, 3rd Edition; Sprague, et al., (Eds. pp. 345-387 American Society of Agronomy Inc., 1988). Methods of introducing expression vectors into plant tissue include the direct infection or co-cultivation of plant cells with *Agrobacterium tumefaciens*, described for example by Horsch et al., *Science*, 227:1229 (1985). Descriptions of *Agrobacterium* vector systems and methods for *Agrobacterium*-mediated gene transfer are provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using a microprojectile media delivery system with a biolistic device or using *Agrobacterium*-mediated transformation. Transformant plants obtained with the protoplasm of the invention are intended to be within the scope of this invention.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed rice plants, using transformation methods as described below to incorporate transgenes into the genetic material of the rice plant(s).

Expression Vectors for Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988); Jones et al., *Mol. Gen. Genet.*, 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci. U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Expression Vectors for Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen. Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/NcoI fragment 5' to the *Brassica napus* ALS3 structural gene (or a nucleotide sequence similar to said Xba1/NcoI fragment), represents a particularly useful constitutive promoter. See PCT application WO96/30530.

C. Tissue-specific or Tissue-preferred Promoters—A tissue-specific promoter is operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981). According to a preferred embodiment, the transgenic plant provided for commercial production of foreign protein is rice. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*. CRC Press, Boca Raton. 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect *Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such As:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content, 1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene; 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., *The Plant Journal* 6:271-282 (1994) and U.S. Pat. No. 5,591,616 issued Jan. 7, 1997. Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Bio/Technology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9:996 (1991). Additionally, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of rice target tissues, expression of the above-described selectable marker genes allows for preferential selection of transformed cells, tissues and/or plants, using regeneration and selection methods now well known in the art. The foregoing methods for transformation would typically be used for producing a transgenic cultivar. The transgenic cultivar could then be crossed, with another (non-transformed or transformed) cultivar, in order to produce a new transgenic cultivar. Alternatively, a genetic trait which has been engineered into a particular rice cultivar using the foregoing transformation techniques could be moved into another cultivar using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar which does not contain that gene. As used herein, "crossing" can refer to a simple X by Y cross, or the process of backcrossing, depending on the context.

Single Gene Conversion

When the term rice plant is used in the context of the present invention, this also includes any single gene conversions of that cultivar. The term single gene converted plant as used herein refers to those rice plants which are developed by a plant breeding technique called backcrossing wherein essentially all of the desired morphological and physiological characteristics of a cultivar are recovered in addition to the single gene transferred into the cultivar via the backcrossing technique. Backcrossing methods can be used with the present invention to improve or introduce a characteristic into the cultivar. The term backcrossing as used herein refers to the repeated crossing of a hybrid progeny back to one of the parental rice plants, the recurrent parent, for that cultivar, i.e., backcrossing 1, 2, 3, 4, 5, 6, 7, 8, 9 or more times to the recurrent parent. The parental rice plant which contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second cultivar (nonrecurrent parent) that carries the single gene of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single transferred gene from the nonrecurrent parent as determined at the 5% significance level when grown in the same environmental conditions.

The selection of a suitable recurrent parent is an important step for a successful backcrossing procedure. The goal of a backcross protocol is to alter or substitute a single trait or characteristic in the original cultivar. To accomplish this, a single gene of the recurrent cultivar is modified or substituted with the desired gene from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Tissue Culture

Further reproduction of rice plants containing the phd allele can occur by tissue culture and regeneration. Tissue culture of various tissues of rice and regeneration of plants therefrom is well known and widely published. For example, reference may be had to Komatsuda, T. et al., Crop Sci. 31:333-337 (1991); Stephens, P. A., et al., *Theor. Appl. Genet.* (1991) 82:633-635; Komatsuda, T. et al., *Plant Cell, Tissue and Organ Culture,* 28:103-113 (1992); Dhir, S. et al., *Plant Cell Reports* (1992) 11:285-289; Pandey, P. et al., *Japan J. Breed.* 42:1-5 (1992); and Shetty, K., et al., *Plant Science* 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce rice plants having the physiological and morphological characteristics of rice plants containing the phd allele.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, pistils, anthers and the like.

The present invention contemplates a rice plant regenerated from a tissue culture of a variety or hybrid plant containing the allele phd of the present invention. As is well known in the art, tissue culture of rice can be used for the in vitro regeneration of a rice plant. Tissue culture of various tissues of rice and regeneration of plants therefrom is well known and widely published. For example, reference may be had to Chu, Q. R., et al., (1999) "Use of bridging parents with high anther culturability to improve plant regeneration and breeding value in rice", *Rice Biotechnology Quarterly* 38:25-26; Chu, Q. R., et al., (1998), "A novel plant regeneration medium for rice anther culture of Southern U.S. crosses", *Rice Biotechnology Quarterly* 35:15-16; Chu, Q. R., et al., (1997), "A novel basal medium for embryogenic callus induction of Southern US crosses", *Rice Biotechnology Quarterly* 32:19-20; and Oono, K., "Broadening the Genetic Variability By Tissue Culture Methods", *Jap. J. Breed.* 33 (Suppl. 2), 306-

307, illus. 1983. Thus, another aspect of this invention is to provide cells which upon growth and differentiation produce rice plants having the physiological and morphological characteristics of rice plants containing allele phd.

Duncan, et al., *Planta* 165:322-332 (1985) reflects that 97% of the plants cultured that produced callus were capable of plant regeneration. Subsequent experiments with both cultivars and hybrids produced 91% regenerable callus that produced plants. In a further study in 1988, Songstad, et al., *Plant Cell Reports* 7:262-265 (1988), reports several media additions that enhance regenerability of callus of two cultivars. Other published reports also indicated that "non-traditional" tissues are capable of producing somatic embryogenesis and plant regeneration. K. P. Rao et al., *Maize Genetics Cooperation Newsletter*, 60:64-65 (1986), refers to somatic embryogenesis from glume callus cultures and B. V. Conger, et al., *Plant Cell Reports*, 6:345-347 (1987) indicates somatic embryogenesis from the tissue cultures of corn leaf segments. Thus, it is clear from the literature that the state of the art is such that these methods of obtaining plants are routinely used and have a very high rate of success.

Rice varieties containing mutant allele phd of the present invention can also be used for transformation where exogenous genes are introduced and expressed by the variety containing allele phd. Genetic variants created either through traditional breeding methods using a line containing allele phd or through transformation of a line containing allele phd by any of a number of protocols known to those of skill in the art are intended to be within the scope of this invention.

The following describes breeding methods that may be used with a rice plant containing allele phd in the development of further rice plants. One such embodiment is a method for developing a progeny rice plant in a rice plant breeding program comprising: obtaining a rice plant, or a part thereof, which comprises allele phd, utilizing said plant or plant part as a source of breeding material and selecting a progeny plant containing allele phd with molecular markers in common with rice plants containing allele phd and/or with morphological and/or physiological characteristics selected from the characteristics listed in Tables 1 through 4. Breeding steps that may be used in the rice plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes rice plants containing allele phd progeny rice plants so that said progeny rice plants are not significantly different for said traits than rice plants containing allele phd as determined at the 5% significance level when grown in the same environment. Using techniques described herein, molecular markers may be used to identify said progeny plant as a plant containing allele phd progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of rice plants containing allele phd may also be characterized through their filial relationship with rice plants containing allele phd, as for example, being within a certain number of breeding crosses of rice plants containing allele phd. A breeding cross is a cross made to introduce new genetics into the progeny, and is distinguished from a cross, such as a self or a sib cross, made to select among existing genetic alleles. The lower the number of breeding crosses in the pedigree, the closer the relationship between rice plants containing allele phd and its progeny. For example, progeny produced by the methods described herein may be within 1, 2, 3, 4 or 5 breeding crosses of rice plants containing allele phd.

The seed of rice plants containing allele phd, the plant produced from the seed, the hybrid rice plant produced from the crossing of the cultivar, hybrid seed, and various parts of the hybrid rice plant and transgenic versions of the foregoing, can be utilized for human food, livestock feed, and as a raw material in industry Deposit Information Rice seeds labeled DW-206 containing the phd mutant allele have been placed on deposit with the American Type Culture Collection (ATCC), 10801 University Boulevard, Manassas, Va. 20110-2209 on Jul. 19, 2007 and having Deposit Accession Number PTA-8541. The "phd" mutant allele is the exact same allele as the DW-206 allele. DW-206 is the formerly used name for the phd mutant allele. Some of the documents submitted to ATCC indicate DW-206 which is the exact same allele as that of the present invention, phd.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A rice seed containing an allele designated phd wherein a representative sample of seed containing said phd allele has been deposited under ATCC Accession No. PTA-8541.

2. A rice plant, or a part thereof, produced by growing the seed of claim 1.

3. A tissue culture of cells or protoplasts produced from the plant of claim 2, wherein said cells or protoplasts of the tissue culture are produced from a plant part selected from the group consisting of leaf, pollen, embryo, cotyledon, hypocotyl, meristematic cell, root, root tip, pistil, anther, flower, stem, glume and panicle.

4. A rice plant regenerated from the tissue culture of claim 3.

5. A method for producing an $F_1$ hybrid rice seed, wherein the method comprises crossing the plant of claim 2 with a different rice plant and harvesting the resultant $F_1$ hybrid rice seed.

6. A hybrid rice seed produced by the method of claim 5.

7. A hybrid rice plant, or a part thereof, produced by growing said hybrid seed of claim 6.

8. A method of producing an herbicide resistant rice plant wherein the method comprises transforming the rice plant of claim 2 with a transgene wherein the transgene confers resistance to an herbicide selected from the group consisting of imidazolinone, sulfonylurea, glyphosate, glufosinate, L-phosphinothricin, triazine and benzonitrile.

9. An herbicide resistant rice plant produced by the method of claim 8.

10. A method of producing an insect resistant rice plant wherein the method comprises transforming the rice plant of claim 2 with a transgene that confers insect resistance.

11. An insect resistant rice plant produced by the method of claim 10.

12. The rice plant of claim 11, wherein the transgene encodes a *Bacillus thuringiensis* endotoxin.

13. A method of producing a disease resistant rice plant wherein the method comprises transforming the rice plant of claim 2 with a transgene that confers disease resistance.

14. A disease resistant rice plant produced by the method of claim 13.

15. A method of producing a rice plant with modified fatty acid metabolism or modified carbohydrate metabolism wherein the method comprises transforming the rice plant of claim 2 with a transgene encoding a protein selected from the group consisting of fructosyltransferase, levansucrase, alpha-amylase, invertase and starch branching enzyme or encoding an antisense of stearyl-ACP desaturase.

16. A rice plant having modified fatty acid metabolism or modified carbohydrate metabolism produced by the method of claim 15.

17. A method of introducing a desired trait into a rice plant containing allele phd wherein the method comprises:
   (a) crossing a rice plant containing allele phd, wherein a representative sample of seed was deposited under ATCC Accession No. PTA-8541, with a plant of another rice cultivar that comprises a desired trait to produce progeny plants wherein the desired trait is selected from the group consisting of male sterility, herbicide resistance, insect resistance, modified fatty acid metabolism, modified carbohydrate metabolism and resistance to bacterial disease, fungal disease or viral disease;
   (b) selecting one or more progeny plants that have the desired trait to produce selected progeny plants;
   (c) crossing the selected progeny plants with the rice plant containing allele phd to produce backcross progeny plants;
   (d) selecting for backcross progeny plants that have the desired trait and the physiological and morphological characteristics of the rice plant containing allele phd to produce selected backcross progeny plants; and
   (e) repeating steps (c) and (d) two times to produce selected third or higher backcross progeny plants that comprise the desired trait and all of the physiological and morphological characteristics of the rice plant containing allele phd as listed in Tables 1, 2, 3, and 4.

18. A plant produced by the method of claim 17, wherein the plant has the desired trait and all of the physiological and morphological characteristics of the rice plant containing allele phd as listed in Tables 1, 2, 3 and 4.

19. The plant of claim 18, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

20. The plant of claim 18, wherein the desired trait is insect resistance and the insect resistance is conferred by a transgene encoding a *Bacillus thuringiensis* endotoxin.

21. The plant of claim 18, wherein the desired trait is modified fatty acid metabolism or modified carbohydrate metabolism and said desired trait is conferred by a nucleic acid encoding a protein selected from the group consisting of fructosyltransferase, levansucrase, alpha-amylase, invertase and starch branching enzyme or encoding an antisense of stearyl-ACP desaturase.

* * * * *